United States Patent
Shiozawa et al.

(10) Patent No.: US 8,155,480 B2
(45) Date of Patent: Apr. 10, 2012

(54) IMAGE PROCESSING APPARATUS AND IMAGE PROCESSING METHOD

(75) Inventors: Hideto Shiozawa, Kawasaki (JP); Tsukasa Sako, Yokohama (JP); Masahiro Abe, Yokohama (JP); Yuichi Nishii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 944 days.

(21) Appl. No.: 12/026,447

(22) Filed: Feb. 5, 2008

(65) Prior Publication Data
US 2008/0187205 A1 Aug. 7, 2008

(30) Foreign Application Priority Data
Feb. 6, 2007 (JP) .................................. 2007-026679

(51) Int. Cl.
*G06K 9/36* (2006.01)
(52) U.S. Cl. ...................................... 382/284; 382/132
(58) Field of Classification Search ............. 348/E5.086, 348/E5.088; 378/98.12; 382/132, 284; 702/8, 702/40, 172
See application file for complete search history.

(56) References Cited

U.S. PATENT DOCUMENTS
3,594,161 A * 7/1971 Kaufman ..................... 430/46.1
2002/0012450 A1 * 1/2002 Tsujii ............................ 382/103

FOREIGN PATENT DOCUMENTS
| JP | 11-197138 A | | 7/1999 |
| JP | 2001-043366 | * | 2/2001 |
| JP | 2001-043366 A | | 2/2001 |
| JP | 2006-034452 | * | 2/2006 |
| JP | 2006-034452 A | | 2/2006 |

* cited by examiner

*Primary Examiner* — Gregory F Cunningham
(74) *Attorney, Agent, or Firm* — Canon U.S.A., Inc. IP Division

(57) ABSTRACT

An image processing apparatus includes a combining unit configured to combine a visible light image obtained by capturing visible light from an object and a radiation image obtained by capturing a radiation ray that has passed through the object, and an image processing unit configured to change a proportion between the visible light image and the radiation image to be combined by the combining unit such that the proportion differs between combinations in a peripheral region and a central region.

12 Claims, 8 Drawing Sheets

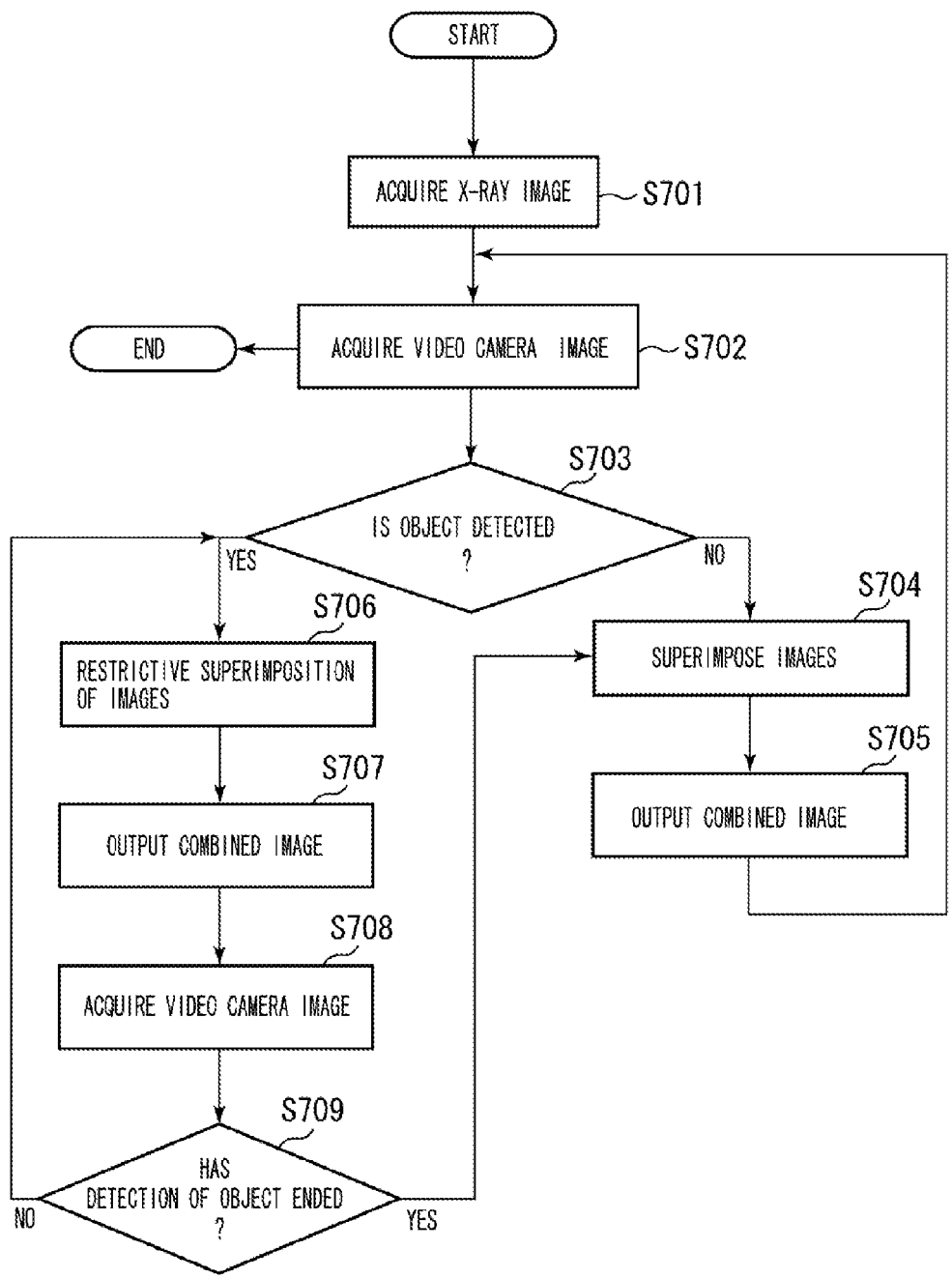

IMAGE PROCESSING APPARATUS AND IMAGE PROCESSING METHOD

BACKGROUND OF THE INVENTION

1. Field of the Invention

The present invention relates to an image processing apparatus configured to use radiation images and visible light images and a method for the same.

2. Description of the Related Art

Existing technology in the field of radiographic X-ray equipment for medical applications facilitates visual identification of an object irradiated with X-rays by generating a combined image from an X-ray image and a video camera image.

For example, in such a method a video camera is placed at a position optically equivalent to an X-ray generation unit, and an image generated by superimposing a video camera image and an X-ray image is displayed on a monitor. The optically equivalent position refers to a set of two positions where an image captured at one of these positions is identical to an image captured at the other position. Generally, a video camera is placed at a position optically equivalent to the position where an X-ray generation unit is placed by using a half mirror.

Japanese Patent No. 3554172 discusses such a method that an X-ray generation unit and a video camera are disposed at substantially the same positions, and a combined image is generated from an X-ray image and a video camera image.

A surgical method is discussed where a surgical tool is used to puncture an object of surgery in the spinal cord after confirmation of a given position using a combined image generated from an X-ray image and a video camera image. Paracentesis, i.e., puncturing with a surgical tool, is one of less invasive surgical methods and imposes less physical burden on the patient because it requires only a smaller portion of the body to be cut out.

With this surgical method, first, an X-ray image is captured by an X-ray imaging apparatus. Then, a video camera is placed at a position that is optically equivalent to an X-ray generation unit of the X-ray imaging apparatus, and a video camera image is captured from the same angle as the X-ray image. A combined image is generated from the video camera image and the X-ray image. The surgeon locates the point of puncture by observing the combined image and marks a position on the object corresponding to the point of puncture. The puncture point thus corresponds to the marked point.

FIG. 8A illustrates a case where a successful puncture can be done in a paracentesis operation that uses a combined image generated from a video camera image and an X-ray image. A half mirror 801 transmits X-rays but reflects visible light. In the setup illustrated in FIG. 8A, an X-ray generation unit 802 and a video camera 803 are placed at positions optically equivalent to each other by using the half mirror 801 to capture an image of an object 804. X-rays emitted from the X-ray generation unit 802 pass through the object 804 and are then detected by an X-ray sensor 805.

In FIG. 8A, an X-ray 806 passes through the center of the object 804. The video camera 803 captures a video camera image of a point 808, and the X-ray sensor 805 captures an X-ray image formed from an X-ray that has passed between the point 808 and a point 809. These two captured images are then superimposed at the center of the combined image. The point 809 is located vertically below the point 808. Therefore, when the object of the paracentesis operation is located between the point 808 and the point 809, the surgical operation can be successfully carried out by marking the position of the point 808 and puncturing from the point 808 vertically downward.

An X-ray 807 illustrated in FIG. 8B passes through an edge of the object 804. As can be seen from FIG. 8B, the X-ray sensor 805 receives the X-ray 807, which has passed between a point 810 and a point 811 of the object 804, to capture an X-ray image. On the other hand, the video camera 803 captures a video camera image of the point 810.

As a result, an edge of the combined image is formed by superimposing the video camera image of the point 810 captured by the video camera 803 and the X-ray image captured by the X-ray sensor 805 from the X-ray that has passed between the point 810 and the point 811.

The point 810 and the point 811 deviate from each other by a distance d in the horizontal direction. The distance d between the corresponding points in an image generated by superimposing a visible light image, such as video camera image, and a radiation image, such as X-ray image, is hereinafter referred to as a positional deviation. When the point 811 is where punctuation is to be done, the surgical tool cannot reach the point 811 by punctuating at the point 810 vertically downward. The difficulty in the paracentesis operation becomes greater as the positional deviation d becomes larger. Thus, it is difficult to reliably locate a correct point of punctuation using a combined image.

SUMMARY OF THE INVENTION

The present invention is directed to enabling a user to determine a positional deviation occurring in a combined image generated from a radiation image and a visible light image.

According to an aspect of the present invention, an image processing apparatus includes a combining unit configured to combine a visible light image obtained by capturing visible light from an object and a radiation image obtained by capturing a radiation ray that has passed through the object, and an image processing unit configured to change a proportion between the visible light image and the radiation image to be combined by the combining unit such that the proportion differs between combinations in a peripheral region and a central region.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 7 illustrates a process flow according to a third embodiment of the present invention.

DETAILED DESCRIPTION OF THE EMBODIMENTS

Various exemplary embodiments, features, and aspects of the invention will be described in detail below with reference to the drawings.

Figure 1:
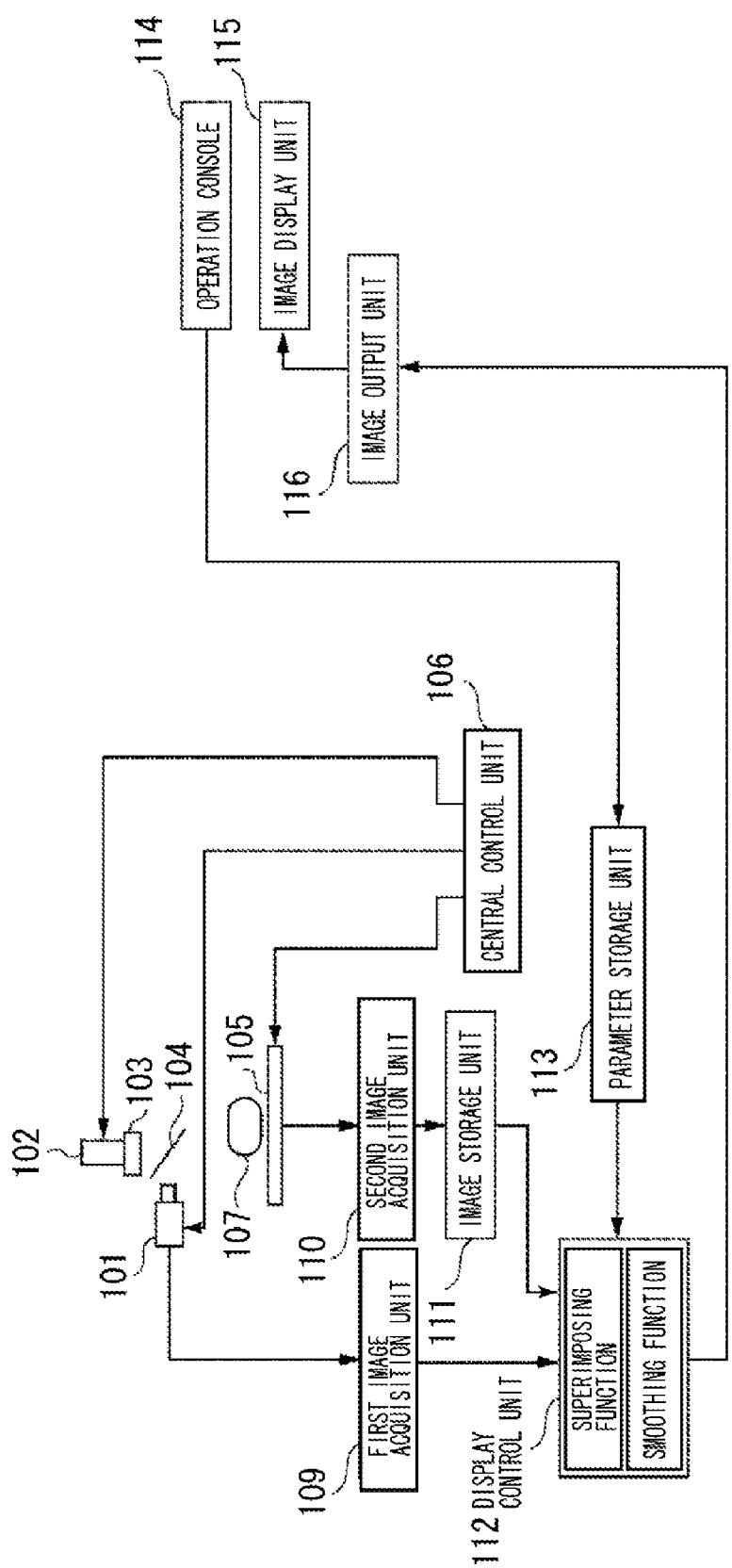
FIG. 1 illustrates a configuration of an apparatus according to a first exemplary embodiment of the present invention.

FIG. 1 illustrates a configuration of an apparatus according to a first exemplary embodiment of the present invention. A process carried out with the configuration described below can be replaced by a process of computer operation.

A video camera 101 is configured to capture an image of visible light. While the present exemplary embodiment uses a video camera to capture an image of visible light, a different type of apparatus can be employed as long as it can capture an image of visible light.

An X-ray generation unit 102 is configured to emit an X-ray in response to a voltage applied to an X-ray bulb incorporated therein. A collimator 103 is configured to adjust the focus of an X-ray. An X-ray generated by the X-ray generation unit 102 is emitted through the collimator 103.

A half mirror 104 transmits an X-ray but reflects visible light. By using the half mirror 104, the video camera 101 and the X-ray generation unit 102 are disposed at optically equivalent positions.

As previously described, the optically equivalent position refers to a set of two positions where an image captured at one of these positions is identical to an image captured at the other position. In FIG. 1, for example, since the half mirror 104 reflects visible light, visible light that would reach the X-ray generation unit 102 in the absence of the half mirror 104 reaches the video camera 101.

Therefore, the video camera 101 can capture the same image as would be captured if the video camera 101 were placed at the position of the X-ray generation unit 102.

The X-ray sensor 105 senses an X-ray emitted by the X-ray generation unit 102 to generate an X-ray image.

While an X-ray is used to capture an image in an exemplary embodiment, the present invention is not limited to an X-ray. Any radiation of wavelengths other than X-ray wavelengths can be used to capture a radiation image.

A central control unit 106 includes a random access memory (RAM) that stores a control program for controlling the operation of capturing an X-ray image and a visible light image, and a central processing unit (CPU) that executes the control program, etc.

The central control unit 106 sends control signals to the X-ray generation unit 102 and the X-ray sensor 105 to enable the X-ray sensor 105 to detect an X-ray generated by the X-ray generation unit 102. The central control unit 106 further sends a control signal to the video camera 101 to enable the video camera 101 to capture an image of visible light.

The object 107 is, for example, a patient to be subjected to a surgical operation, whose X-ray image is captured by using the X-ray generation unit 102 and the X-ray sensor 105, and whose visible light image is captured by using the video camera 101.

A first image acquisition unit 109 includes an interface, such as Universal Serial Bus (USB) or Institute of Electrical and Electronic Engineers (IEEE) 1394 interface, and acquires a video camera image captured by the video camera 101.

A second image acquisition unit 110 includes an interface, such as USB or IEEE 1394 interface, and acquires an X-ray image captured by the X-ray sensor 105.

An image storage unit 111 includes a hard disk, a flash memory, etc. The image storage unit 111 receives an X-ray image from the second image acquisition unit 110 and stores the image data in the hard disk or the flash memory. Since roentgenography imposes a health hazard to the object 107, repetition thereof should be avoided. In order to avoid repetition, an X-ray image acquired by roentgenography is recorded in the image storage unit 111.

A display control unit 112 includes, for example, a RAM in which a processing program is stored, and a CPU that executes the processing program for carrying out a superimposing process and a smoothing process. The display control unit 112 has a superimposing function for superimposing images to generate a combined image, thus serving as a combined image generating unit. The display control unit 112 also has a smoothing function for smoothing the image. The display control unit 112 can also share the CPU and the RAM with the central control unit 106. Separate CPUs and RAMs can be provided for different functions, or the same CPU and RAM can be used in common to carry out the superimposing process and the smoothing process. The display control unit 112 acquires a video camera image from the first image acquisition unit 109 and acquires an X-ray image from the image storage unit 111 to carry out the superimposing process and the smoothing process on the video camera image and the X-ray image.

A parameter storage unit 113 includes a storage device, such as flash memory. The parameter storage unit 113 stores superimposing process parameters to be used by the display control unit 112 in the superimposing function and stores smoothing process parameters to be used in the smoothing function. The superimposition process parameters include a parameter that represents a proportion between the X-ray image and the video camera image to be superimposed, and a parameter that represents a region to be superimposed. The smoothing process parameter represents the intensity of the smoothing operation.

The display control unit 112 carries out the superimposing process and the smoothing process by acquiring the superimposing process parameters and the smoothing process parameters from the parameter storage unit 113. Specific procedures of carrying out the superimposing process and the smoothing process will be described below with reference to the flowchart illustrated in FIGS. 2A and 2B.

An operation console 114 includes input devices, such as a keyboard and a mouse, operable by a user. While the parameter storage unit 113 stores the superimposing process parameters and the smoothing process parameters that have been set in advance, these parameters can be altered by the user via the operation console 114.

An image display unit 115 includes an image display device, such as a video monitor, to display the received image. An image output unit 116 includes an image graphic board, which receives an image from the display control unit 112, converts the image data into a data format that can be displayed on the image display unit 115, and sends the image data to the image display unit 115.

A zoom adjustment operation of the video camera 101 will be described below. The video camera 101 and the X-ray generation unit 102 are placed at optically equivalent positions as described above. Therefore, zoom adjustment of the video camera 101 can be carried out by making reference to an image of the X-ray sensor 105 contained in the image captured by the video camera 101.

Figure 3:
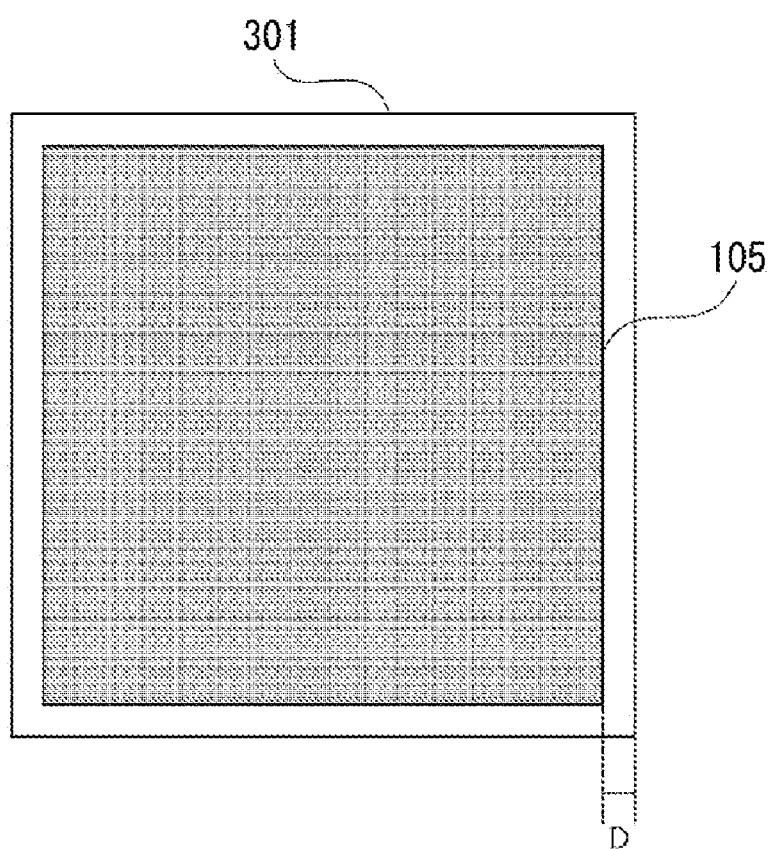
FIG. 3 illustrates an example of an image obtained during zoom adjustment according to the first exemplary embodiment of the present invention.

FIG. 3 illustrates an image of the X-ray sensor 105 captured within a video camera image 301. In a zoom state illustrated in FIG. 3, an image of the X-ray sensor 105 is captured smaller by a width D relative to the entire video camera image 301.

In order to correctly superimpose a video camera image and an X-ray image, it is desirable that the outline of the video camera image 301 and the outer edge of the X-ray sensor 105 coincide with each other, i.e., the width D of the positional deviation between the video camera image 301 and the image of the X-ray sensor 105 is nearly zero.

In an exemplary embodiment, the central control unit 106 processes an image captured by the video camera 101, calculates the amount of zoom adjustment, and performs zoom adjustment. Alternatively, the user can perform zoom adjustment manually while checking an image captured by the video camera 101.

Figure 2A:
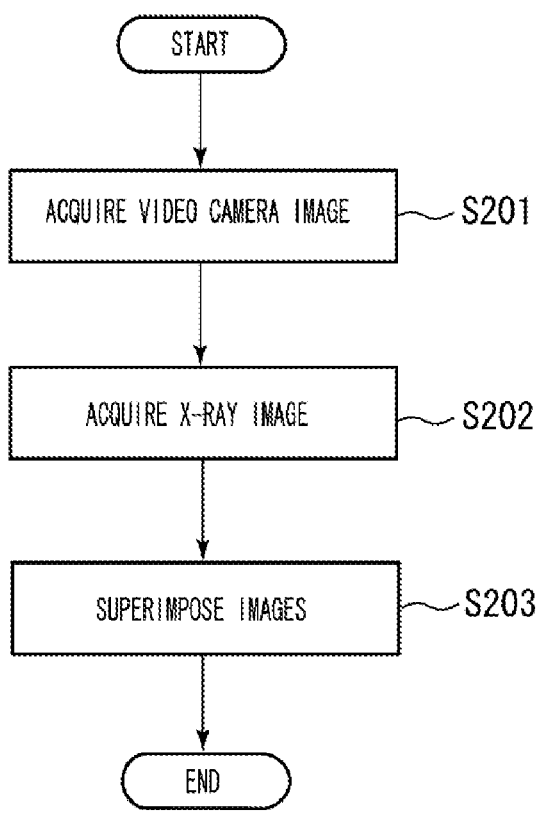
FIGS. 2A and 2B are flowcharts of a process according to the first exemplary embodiment of the present invention.
Figure 2B:
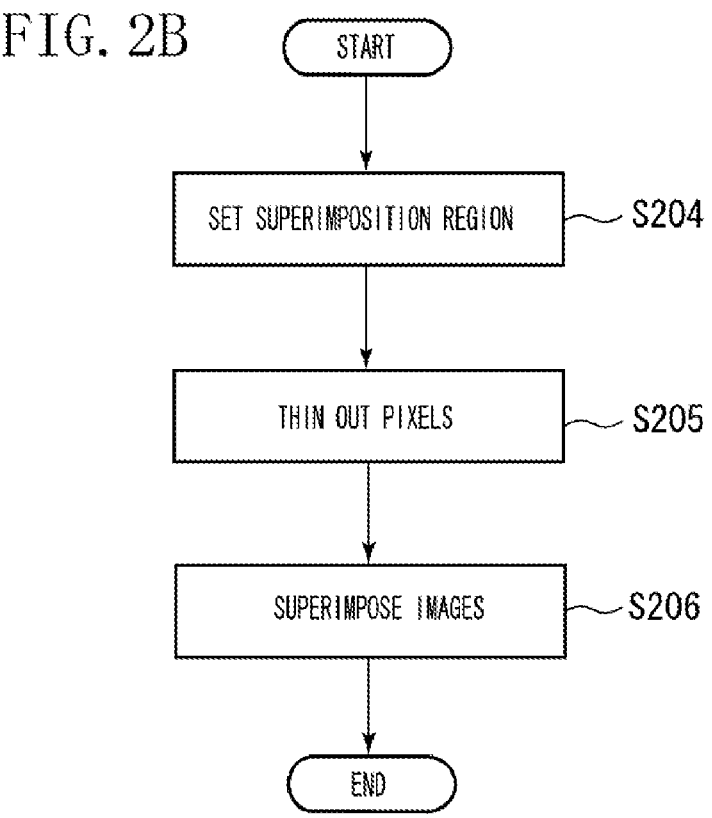

Now, the procedure for carrying out the process using the apparatus illustrated in FIG. 1 will be described below with reference to the flowcharts illustrated in FIGS. 2A and 2B. The operations of the flowcharts illustrated in FIGS. 2A and 2B are carried out by the various units illustrated in FIG. 1 under the control of the central control unit 106 and the display control unit 112 illustrated in FIG. 1.

In step S201, the video camera 101 captures a video camera image of the object 107 via the half mirror 104 according to a control instruction from the central control unit 106. The captured video camera image is sent to the first image acquisition unit 109.

In step S202, the X-ray generation unit 102 irradiates the object 107 with X-rays according to a control instruction from the central control unit 106, and the X-ray sensor 105 captures an X-ray image from X-rays that have passed through the object 107. The captured X-ray image is sent to the second image acquisition unit 110. The X-ray image sent to the second image acquisition unit 110 is then stored in the image storage unit 111.

Figure 4A:
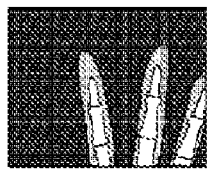
FIGS. 4A through 4D are examples of images displayed in the first exemplary embodiment of the present invention.
Figure 4B:
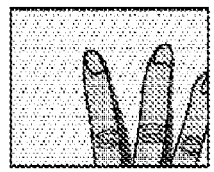

In step S203, the display control unit 112 carries out the superimposing operation. The superimposing operation is a process for superimposing a first image on a second image to generate a combined image from the first image and the second image. In an exemplary embodiment, the display control unit 112 superimposes the video camera image acquired in step S201 on the X-ray image acquired in step S202 to generate a combined image. An example of the video camera image acquired in step S201 is illustrated in FIG. 4B, and an example of the X-ray image acquired in step S202 is illustrated in FIG. 4A. In an exemplary embodiment, the display control unit 112 superimposes the video camera image on the X-ray image to generate a combined image. However, the display control unit 112 can superimpose the X-ray image on the video camera image to generate a combined image.

Figure 4C:
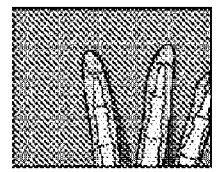
Figure 8A:
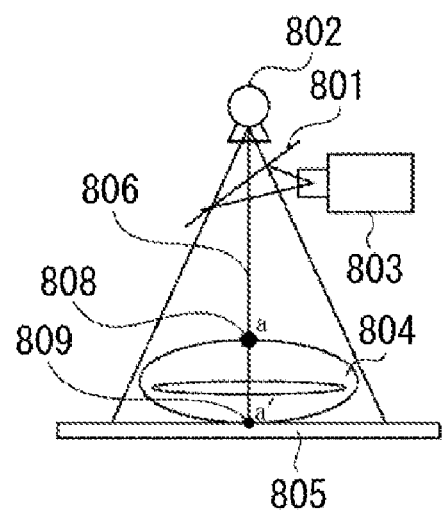
FIGS. 8A and 8B illustrate a conventional technical problem.
Figure 8B:
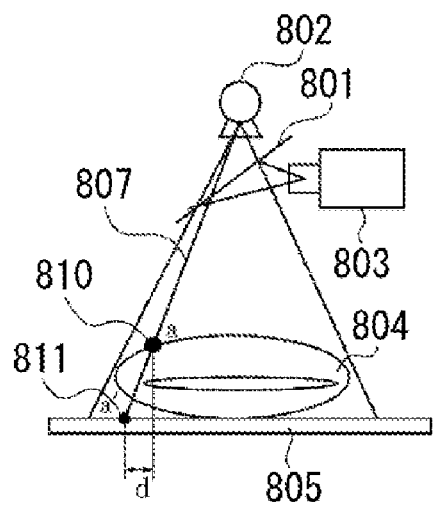

The image illustrated in FIG. 4C is a combined image generated by superimposing the video camera image illustrated in FIG. 4B on the X-ray image illustrated in FIG. 4A. However, there is a large positional deviation in a peripheral region as described above in FIG. 8B. Accordingly, it is difficult to locate a correct point to puncture. The positional deviation mentioned here refers to the distance between corresponding points in a visible light image, such as a video camera image, and a radiation image, such as an X-ray image, when both images are superimposed one on another.

Accordingly, in an exemplary embodiment, the display control unit 112 extracts from the video camera image a region in which a positional deviation between the X-ray image and the video camera image is small and superimposes only the extracted region on the X-ray image to generate a combined image.

FIG. 2B illustrates a method of superimposing images according to the present embodiment.

In step S204 and step S205, the display control unit 112 functions as an arithmetic operation unit configured to obtain information on the positional deviation and functions as an image processing unit configured to process an image based on the information on the positional deviation.

In step S204, the display control unit 112 functions as an arithmetic operation unit configured to obtain information on the positional deviation and determines a region in which a positional deviation between corresponding points in the X-ray image and the video camera image is small. A region in which the positional deviation is small can be extracted by dividing the video camera image into a plurality of small regions. After dividing the video camera image, the display control unit 112 calculates an angle of X-ray irradiation relative to each region of the video camera image based on the distance between the X-ray generation unit 102 and the X-ray sensor 105 and the aperture setting of the X-ray generation unit 102. Then, the display control unit 112 calculates the positional deviation in each region based on the depth of the object 107 and the tangent of the calculated irradiation angle.

The display control unit 112 then functions as a region setting unit configured to designate a set of regions to be superimposed having a predetermined shape. The designated set of regions to be superimposed has small calculated positional deviations. More specifically, the display control unit 112 sets a pixel value to zero in a region in which the positional deviation is greater than a predetermined value. Alternatively, as a simpler method, the display control unit 112 can designate a region of a predetermined size from the center of the image as the region of small positional deviation, by making use of the fact that the positional deviation is relatively small in the central region. When designating a region of small positional deviation, the display control unit 112 can also use a parameter that indicates a predetermined superimposition region included in the superimposing process parameters.

In step S205, the display control unit 112 thins out pixels from the video camera image that has been acquired from the first image acquisition unit 109 according to a combination ratio included in the superimposing process parameters obtained from the parameter storage unit 113. For example, when the combination ratio is set to 50%, a half of the pixels included in the video camera image are randomly discarded.

In step S206, the display control unit 112 carries out the superimposing operation. The display control unit 112 compares a pixel of the video camera image and a pixel of the X-ray image obtained from the image storage unit 111. In the comparison process, the display control unit 112 determines whether the pixel of the video camera image is located at the same position as that of the pixel of the X-ray image. When the pixels are located at the same position, the display control unit 112 assigns the pixel value of the video camera image to the pixel of the combined image. When the pixels are not located at the same position, the display control unit 112 assigns the pixel value of the X-ray image to the pixel of the combined image. All pixel values of the combined image are determined in this process, so that the combined image is generated according to the combination ratio. The combined image thus generated is displayed on the display unit 115. As the combined image is displayed, the user is enabled to know the positional deviation and readily determine whether a point is appropriate for puncture.

Figure 4D:

Since the positional deviation is generally smaller in the central portion of the image as previously described, the combined image has the X-ray image superimposed only in the central portion as illustrated in FIG. 4D. As the X-ray image is superimposed only in the central portion where the positional deviation is smaller, the user is enabled to know the positional deviation and determine a region where puncture can be appropriately carried out.

Figure 5A:
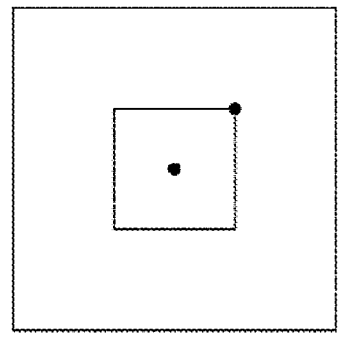
FIGS. 5A and 5B illustrate a method of designating a superimposition region according to the first exemplary embodiment of the present invention.
Figure 5B:
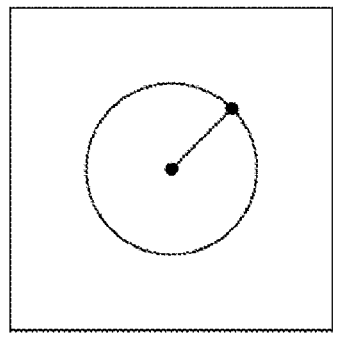

In the process illustrated in FIG. 2B, the display control unit 112 estimates the positional deviation and extracts the superimposition region. Alternatively, the display control unit 112 can determine the superimposition region based on an instruction from a user. For example, when the user uses a mouse or other pointer to designate two points in the image displayed on the display unit 115, the display control unit 112 designates a rectangular region having vertexes located at the selected two points as the superimposition region. When the center of the superimposition region is set at the center of the image in advance, the user can designate a rectangular region as the superimposition region by selecting one point within the image. The rectangular region is set similar in shape to the outer frame of the image as illustrated in FIG. 5A. The superimposition region can also be set as a circular region rather than rectangle. In the case of a circular region, the superimposition region is set as a circle having the center located at the center of the image and a radius equal to the distance between the point having the coordinates designated by the user and the center of the image, as illustrated in FIG. 5B.

In the process described above, the display control unit 112 extracts from the video camera image a region in which a positional deviation between the X-ray image and the video camera image is small and superimposes only the extracted region on the X-ray image to generate a combined image. Alternatively, the display control unit 112 can generate a combined image by superimposing the video camera image on only the central portion of the X-ray image by employing a smoothing operation, without extracting the superimposition region.

The method of a smoothing operation will be described below. A smoothing operation refers to an operation of transforming an image into a blurred image having less variation in density. In an exemplary embodiment, the display control unit 112 carries out a smoothing operation on the peripheral region of the combined image to blur the peripheral region, in which the positional deviation between the video camera image and the X-ray image is great.

Before carrying out the smoothing operation, the display control unit 112 sets a range to which the smoothing operation is to be applied, similar to the setting of the superimposition region. The range to which the smoothing operation is applied can be set either by using a parameter that indicates a superimposition region that has been set in advance, or by following an instruction from a user. After setting the range to which the smoothing operation is applied, the smoothing operation is carried out on this range. Various methods of smoothing have been proposed. For example, a mean pixel value of surrounding pixels can be calculated for each pixel in the peripheral region of the image, followed by alteration of each pixel to the mean pixel value, thereby carrying out the smoothing operation. By carrying out the smoothing operation as described above, a region of the combined image in which there is a large positional deviation between the video camera image and the X-ray image can be blurred.

The procedure described above generates a combined image that enables recognition of the positional deviation. With the combined image enabling recognition of the positional deviation, the user is enabled to know the positional deviation and thus to readily determine whether a point is appropriate for puncture.

A second exemplary embodiment of the present invention will be described below. An apparatus according to the second exemplary embodiment has a similar configuration as that of the first exemplary embodiment, thus, a detailed description is omitted herein. A difference from the first embodiment is that the combined image is divided into a plurality of regions and different superimposition operations or smoothing operations are applied to the respective regions.

Figure 6A:
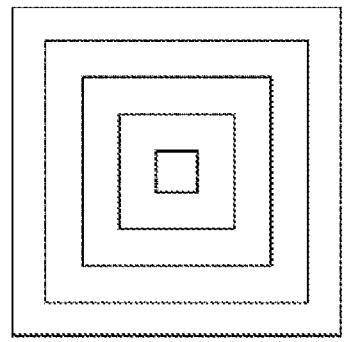
FIGS. 6A and 6B illustrate examples of dividing an image region according to a second exemplary embodiment of the present invention.
Figure 6B:
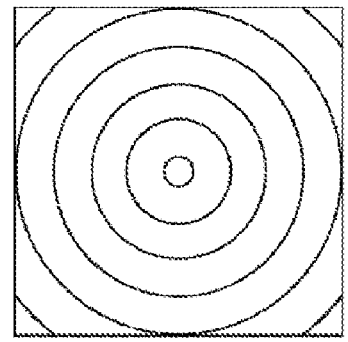

Examples of division of the combined image are illustrated in FIGS. 6A and 6B. FIG. 6A illustrates a division into rectangular regions and FIG. 6B illustrates a division into circular regions. In FIGS. 6A and 6B, the combined image is divided into a plurality of regions arranged concentrically from the center toward the periphery.

In an exemplary embodiment, the display control unit 112 applies different superimposition operations or smoothing operations to the plurality of regions created by division.

First, the method of superimposition according to the present embodiment will be described. In the process of superimposition according to the first embodiment, the display control unit 112 superimposes the video camera image on only the central region of the X-ray image. In the present embodiment, a proportion of the video camera image to be superimposed is changed from region to region of division. More specifically, the display control unit 112 sets a proportion of superimposition between the X-ray image and the video camera image in the central region to a:b. When a portion other than the central region is divided into n regions, the display control unit 112 sets a proportion of superimposition between the X-ray image and the video camera image in the i-th region from the central region according to the following equation (1):

$$a + \frac{b}{n}i : b - \frac{b}{n}i \qquad (1)$$

When the proportion of superimposition is changed according to equation (1), the percentage of the video camera image becomes smaller as the region comes closer to the periphery of the image. Thus, the proportion of superimposition in the outermost region become 1:0, which means the X-ray image without the video camera image superimposed thereon. When the proportion of the video camera image to be superimposed is decreased stepwise toward the outside, the user can distinguish a portion in which the positional deviation between the video camera image and the X-ray image is small and a portion in which the positional deviation is large, in a stepwise manner. When superimposing the video camera image on the X-ray image, the proportion of superimposition between the X-ray image and the video camera image can be inverted.

Next, a method of smoothing according to the present embodiment will be described below. In the smoothing process, the display control unit 112 first generates a combined image from the video camera image and the X-ray image without restriction on the superimposition region as illustrated in FIG. 4C.

The combined image thus generated is divided into regions. Among these regions, the region located at the center of the image is not subjected to smoothing, and a region located at a greater distance from the center of the image is subjected to a higher intensity of smoothing, thereby applying a stepwise smoothing operation to the image. The intensity of smoothing can be increased by using a wider range of surrounding pixels when calculating each mean pixel value during the smoothing operation.

A stepwise smoothing operation can also be carried out by using, for example, a smoothing filter based on equation (1) to determine the intensity of smoothing. The intensity of smoothing can also be determined based on an instruction from a user.

When regions located at a greater distance from the center of the image are subjected to an intensity of smoothing that is decreased stepwise as described above, the user can distinguish a portion in which the positional deviation between the video camera image and the X-ray image is small and a portion in which the positional deviation is large, in a stepwise manner.

An apparatus according to a third exemplary embodiment of the present invention has a similar configuration as that of the first exemplary embodiment illustrated in FIG. 1, and thus a detailed description is omitted herein. A difference from the first embodiment is that the display control unit 112 operates as an object detecting unit, i.e., the display control unit 112 has an object detecting function that detects object data. The display control unit 112 also has an object recognizing function. The object detecting function and the object recognizing function are part of the functions of the display control unit 112, and are achieved by the CPU executing control programs stored in the RAM of the display control unit 112.

The object detecting function can find a predetermined object in an image by processing the video camera image based on object data of the predetermined object (e.g., a human hand) stored in the RAM or the like. The object recognizing function can determine whether the predetermined object is shown in an image based on a difference image made from a plurality of video camera image data stored in the RAM, etc.

The object detecting function can detect an image of the user's hand in the video camera image. When the user carries out a surgical operation or marking, the user's hand is captured within the video camera image. When the object detecting function detects the hand, it assumes the user will carry out a surgical operation or marking. When the user will carry out a surgical operation or marking, a superimposition region of small positional deviation is extracted from the video camera image and is then superimposed on the X-ray image. The extracted superimposition region makes it easier to distinguish a portion in which the positional deviation between the video camera image and the X-ray image is small and a portion in which the positional deviation is large.

The object recognizing function also determines from the difference image of a plurality of images whether an object is shown. Accordingly, the object recognizing function can determine whether a moving object is shown in the video camera image by generating a difference image between the video camera image obtained prior to the user's hand being captured and the video camera image obtained when the user's hand is captured. When the object is not recognized, it can be presumed that the inclusion of the user's hand in the video camera image has ended. When the inclusion of the user's hand in the image has ended, there is no need to restrict a region to be superimposed. Therefore, the display control unit 112 superimposes the video camera image on the X-ray image without restricting the region to be superimposed, so that the image becomes one that makes it easier for the user to recognize the entire object. FIG. 7 illustrates a flowchart of a process for superimposing images according to an exemplary embodiment. The steps included in the flowchart illustrated in FIG. 7 are carried out by the functions of the apparatus illustrated in FIG. 1. The flowchart illustrated in FIG. 7 will be described, for example purposes, with the user's hand as an object to be detected.

In step S701, a signal detected by the X-ray sensor 105 is acquired as an X-ray image by the second image acquisition unit 110, and the X-ray image is stored in the image storage unit 111.

In step S702, the first image acquisition unit 109 acquires a video camera image that has been captured by the video camera 101. If the video camera image cannot be acquired, the process is terminated, i.e., the flow goes to END.

When the video camera image has been acquired, the process proceeds to step S703.

In step S703, the object detecting function of the display control unit 112 determines whether the video camera image includes an image of the user's hand. In this determination, modeling data of the user's hand is used to determine whether the video camera image includes the image of the user's hand.

If the user's hand is not detected (NO in step S703), the process proceeds to step S704. If the user's hand is not detected, this indicates that the user's hand has not been captured by the video camera 101. Therefore, in step S704, the display control unit 112, which functions as the image processing unit, does not perform the smoothing process or the restriction of a superimposition region, and generates a combined image by superimposing the entire video camera image on the X-ray image.

In step S705, the object detecting function of the display control unit 112 sends the combined image generated in step S704 to the image output unit 116, and the display unit 115 then displays the combined image. The combined image displayed is such as the one illustrated in FIG. 4C, and the user can observe an image formed by superimposition on the entire region. After displaying the combined image, the process proceeds to step S702.

On the other hand, if the user's hand is detected (YES in step S703), the process proceeds to step S706. If the user's hand is detected in step S703, this indicates that the user is going to carry out some operation, such as surgery or marking. In step S706, the display control unit 112, which functions as the image processing unit, generates a combined image by using a method such as those described above to superimpose only a region of the video camera image in which the positional deviation is small on the X-ray image. Alternatively, the display control unit 112 applies a smoothing operation to a peripheral region, in which the positional deviation is large.

In step S707, the display control unit 112 sends the combined image to the image output unit 116, and the display unit 115 then displays the combined image. The combined image that is displayed does not have the X-ray image and the video camera image superimposed in the peripheral region of the displayed image, so that the user can distinguish a region having a large positional deviation and a region having a small positional deviation.

In step S708, similar to step S702, the first image acquisition unit 109 acquires an image captured by the video camera 101.

In step S709, the object recognizing function of the display control unit 112 compares the video camera image acquired in step S708 and the image captured in step S703 obtained when the user's hand is not detected. Through comparison of the images, the display control unit 112 recognizes the user's hand captured in the video camera image, and also determines whether the recognized object has disappeared from the image. As a method for the determination, for example, a difference image is generated from the image obtained before the object is detected in step S703 and the video camera image acquired in step S708. If the difference of the difference image is less than or equal to a given threshold, this indicates that the user's hand has disappeared from the image. If the inclusion of the user's hand in the image has ended (YES in step S709), it can be assumed that a surgical operation or marking operation will not be carried out. Accordingly, the process proceeds to step S704. On the other hand, if the inclusion of the user's hand in the image has not ended (NO in step S709), there remains the possibility that a surgical operation or marking operation will be carried out, and the process returns to step S706.

In the procedure described above, a normal superimposing operation is carried out when surgery, etc. is not to be carried out according to the user's instruction, and, therefore, a wider observation region is provided to make it easier for the user to diagnose. If surgical operations, etc. are to be carried out, restrictive superimposition of images can prevent or reduce malpractice by medical staff related to the superimposition of images.

Thus, advantages can be provided to a user engaged in surgery by altering the way images are processed depending on whether the object detecting function has detected an object as in the procedure from step S701 through step S709.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2007-026679 filed Feb. 6, 2007, which is hereby incorporated by reference herein in its entirety.

What is claimed is:

1. An image processing apparatus comprising:
a combining unit configured to combine a visible light image obtained by capturing visible light from an object and a radiation image obtained by capturing radiation rays that have passed through the object; and
an image processing unit configured to perform electronic image processing to change a proportion between the visible light image and the radiation image to be combined by the combining unit such that the proportion differs between combinations in a peripheral region and a central region.

2. The image processing apparatus according to claim 1, further comprising a display unit configured to display a combined image processed by the image processing unit.

3. The image processing apparatus according to claim 1, wherein the image processing unit sets to zero, a pixel value of a pixel in the visible light image whose positional deviation from the radiation image is greater than a predetermined value.

4. The image processing apparatus according to claim 1, wherein the image processing unit reduces the proportion of a pixel in the visible light image according to an increase of a positional deviation of the pixel from the radiation image.

5. The image processing apparatus according to claim 1, wherein the image processing unit sets to zero, a pixel value of a pixel in the radiation image whose positional deviation from the visible light image is greater than a predetermined value.

6. The image processing apparatus according to claim 1, wherein the image processing unit reduces the proportion of a pixel in the radiation image according to an increase of a positional deviation of the pixel from the visible light image.

7. The image processing apparatus according to claim 1, further comprising a setting unit configured to set a region having a predetermined shape based on a position of a pixel in which a positional deviation between the visible light image and the radiation image is smallest among pixels of a combined image generated by the combining unit,
wherein the image processing unit sets to zero, pixel values of pixels outside a set region among the pixels of the combined image.

8. The image processing apparatus according to claim 1, further comprising a setting unit configured to set a region having a predetermined shape based on a position of a pixel in which a positional deviation between the visible light image and the radiation image is smallest among pixels of a combined image generated by the combining unit,
wherein the image processing unit performs a smoothing operation on pixels outside a set region among the pixels of the combined image.

9. The image processing apparatus according to claim 8, wherein the image processing unit increases intensity of a smoothing operation to pixels outside the set region according to an increase of the positional deviation between the visible light image and the radiation image.

10. The image processing apparatus according to claim 1, further comprising an object detecting unit configured to detect object data based on the visible light image,
wherein, when the object detecting unit detects the object data, the image processing unit processes at least one visible light image obtained prior to being combined by the combining unit, radiation image obtained prior to being combined by the combining unit, and a combined image generated by the combining unit based on information on a positional deviation between the visible light image and the radiation image.

11. A method comprising:
combining a visible light image obtained by capturing visible light from an object and a radiation image obtained by capturing radiation rays that have passed through the object; and
performing electronic image processing, using an image processing unit, to change a proportion between the visible light image and the radiation image to be combined by the combining step such that the proportion differs between combinations in a peripheral region and a central region.

12. A non-transitory computer-readable medium storing computer-readable instructions, the computer-readable instructions causing a computer to perform a method comprising:
combining a visible light image obtained by capturing visible light from an object and a radiation image obtained by capturing radiation rays that have passed through the object; and
changing a proportion between the visible light image and the radiation image to be combined by the combining step such that the proportion differs between combinations in a peripheral region and a central region.

* * * * *